US00PP12215P2

(12) United States Plant Patent
Glicenstein

(10) Patent No.: US PP12,215 P2
(45) Date of Patent: Nov. 20, 2001

(54) CHRYSANTHEMUM PLANT NAMED 'BOLD YOFELICIA'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/478,446

(22) Filed: Jan. 6, 2000

(51) Int. Cl.[7] ..... A01H 5/00
(52) U.S. Cl. ..... Plt./286
(58) Field of Search ..... Plt./286, 297, 298

(56) References Cited

PUBLICATIONS

Datta, 1994, "Sensitivity of Mutant Genotypes of Chrysanthemums to Gamma Rays", J. Nuclear Agric. Biol., 23(4):251–254.*
"Mutation Studies on Chrysanthemum", NBRI Newsletter, 1989, 16(1):2–3.*
Datta, 1991, "Evaluation of Recurrent Irradiation on Vegetatively Propagated Ornamentals: Chrysanthemum", J. Nuclear Agric. Biol., 20(2):81–86.*
Banerji, et al., 1990, "Induction of Sometic Mutations in Chrysanthemum Cultivar 'Anupam'", J. Nuclear Agric. Biol., 19:252–256.*
Datta, 1985, "Gamma Ray Induced Mutant of a Mutant of Chrysanthemum", J. Nuclear Agric. Biol., vol. 14:131–133.*
Gosling, ed., 1979, "The Chrysanthemum Manual—6th Edition", The National Chrysanthemum Society, Essex Telegraph Press, Ltd., London, pp. 329–336.*
Broertjes, et al., 1978, "Application of Mutation Breeding Methods in the Improvement of Vegetatively Propagated Crops", Elsevier Sci. Pub. Co., New York, pp. 162–175.*
Gupta, et al., 1978, "Mutation Breeding of Chrysanthemum. II. Detection of Gamma Ray Induced Mutations in vM2", J. Nuclear Agric. Biol. 7(2):50–54.*
Glazurira, et al., 1977, "Use of the Method of Artificial Mutagenesis in the Breeding of Flower Crops", Cytology and Genetics, vol. 11(3):42–45.*
Das, et al., 1977, "Improvement of Some Vegetatively Propagated Ornamentals by Gamma Radiation", Indian J. Horticulture, 34(2):169–174.*
Dowrick, et al., 1966, "The Induction of Mutations in Chrysanthemum Using X– and Gamma Radiation", Euphytica, 15:204–210.*
Broertjes, 1966, Mutation Breeding of Chrysanthemums, Euphytica, 158156–162.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Bold Yofelicia', characterized by its uniformly mounded plant habit; freely branching growth habit; uniform and early flowering; daisy-type inflorescences that are about 5.2 cm in diameter; attractive purple ray florets and bright yellow disc florets; numerous inflorescences per plant; and excellent garden performance.

1 Drawing Sheet

BACKGROUND OF THE INVENTION

The present invention relates to a new and distinct cultivar of Chrysanthemum plant, botanically known as *Dendranthema grandiflora* and hereinafter referred to by the cultivar name Bold Yofelicia.

The new Chrysanthemum is a product of a mutation induction breeding program conducted by the Inventor in Fort Myers, Fla., and Salinas, Calif. The objective of the program is to create new Chrysanthemum cultivars with inflorescences with desirable inflorescence forms, attractive floret colors and good garden performance.

The new Chrysanthemum originated by exposing unrooted cuttings of the Chrysanthemm cultivar Felicia, disclosed in U.S. Plant Pat. No. 9,809, to gamma-ray radiation in June, 1995, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the Inventor as a single flowering plant within this population in February 1996. The selection of this plant was based on its desirable inflorescence form, attractive ray floret color and excellent garden performance.

Asexual reproduction of the new cultivar by terminal cuttings taken in a controlled environment in Salinas, Calif. has shown that the unique features of this new Chrysanthemum are stable and reproduced true to type in successive generations.

SUMMARY OF THE INVENTION

The cultivar Bold Yofelicia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bold Yofelicia'. These characteristics in combination distinguish 'Bold Yofelicia' as a new and distinct cultivar:

1. Uniformly mounded plant habit.
2. Freely branching, dense, full plants.
3. Uniform and early flowering.

4. Daisy-type inflorescences that are about 5.2 cm in diameter.

5. Attractive purple ray florets and bright yellow disc florets.

6. Numerous inflorescences per plant.

7. Excellent garden performance.

Compared to plants of the parent cultivar, Felicia, plants of the new Chrysanthemum flower earlier under artificially-manipulated photoperiodic conditions and differ in ray floret color as plants of 'Felicia' have pink-colored ray florets.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which more accurately describe the actual colors of the new Chrysanthemum.

The photograph at the top of the sheet comprises a top perspective view of a typical flowering plant of 'Bold Yofelicia'.

The photograph at the bottom of the sheet comprises a close-up view of typical inflorescences of the cultivar 'Bold Yofelicia'.

DETAILED BOTANICAL DESCRIPTION

In the following description, color references are made to The Royal Horticultural Society Colour Chart except where general terms of ordinary dictionary significance are used. The following observations and measurements describe plants grown in Pendelton, S.C., under conditions which approximate those generally used in commercial garden Chrysanthemum production. One rooted cutting was planted in a 15-cm container on Jul. 26, 1999 and plants were grown under natural season conditions. Plants were not pinched, that is, the terminal apex was not removed to enhance branching. Measurements and numerical values represent averages for typical flowering plants.

Botanical classification: *Dendranthema grandiflora* cultivar Bold Yofelicia.

Commercial classification: Daisy-type garden chrysanthemum.

Parentage: Induced mutation of *Dendranthema grandiflora* cultivar Felicia, disclosed in U.S. Plant Pat. No. 9,809.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle; mounded plant form. Stems initially upright, then outwardly spreading giving a uniformly mounded appearance to the plant. Freely branching with lateral branches potentially developing at every node.

*Plant height.*—About 31 cm.

*Plant spread.*—About 42 cm.

*Stems.*—Texture: Pubescent. Color: 146A.

*Foliage description.*—Leaf arrangement: Atlernate. Length: About 5.2 cm. Width: About 4.6 cm. Apex: Cuspidate. Base: Mostly truncate. Margin: Palmately lobed, sinuses mostly divergent. Texture: Upper surface sparsely pubescent; lower surface moderately pubescent. Veins prominent on lower surface. Petiole length: About 1.3 cm. Petiole diameter: About 3.5 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Daisy-type inflorescence form with elongated oblong-shaped ray florets. Inflorescences borne on teminals above foliage, arising from leaf axils. Disk and ray florets arranged acropetally on a capitulum. About four inflorescence per lateral; about 120 inflorescenes per plant.

*Flowering response.*—Under natural season conditions, plants flower in the autumn about 66 days after planting.

*Inflorescence bud.*—Height: About 5 mm. Diameter: About 7 mm. Color: Close to 143A.

*Inflorescence size.*—Diameter: About 5.2 cm. Depth (height): About 1.3 cm. Diameter of disc: About 1.5 cm.

*Ray florets.*—Shape: Elongated oblong; mostly horizontal. Length: About 1.5 cm. Width: About 5 mm. Apex: Rounded to emarginate. Margin: Entire. Texture: Smooth, glabrous, satiny; iridescent. Orientation: Initially upright, then perpendicular to the peduncle. Number of ray florets per inflorescence: About 42. Color: When opening, upper surface: Purple, 70A. When opening, lower surface: 75A to 75B; base, white. Opened inflorescence, upper surface: Purple, close to 61A to 71A and 70A; fading to close to 78A to 78B. Opened inflorescence, lower surface: Close to 71A; longitudinal white stripes; base, white.

*Disc florets.*—Shape: Tubular, apex dentate. Length: About 5 mm. Width, apex and base: About 1 mm. Number of disc florets per inflorescence: About 102. Color: Immature: Close to 151A. Mature: Apex: 12A. Mid-section: Close to 154C to 154D. Base: White.

*Peduncle.*—Aspect: Flexible, angled about 50° to the stem. Length: First peduncle: About 5.6 cm. Fourth peduncle: About 8.6 cm. Diameter: About 2 mm. Texture: Pubescent. Color: 146A; some anthocyanin at lower nodes.

*Reproductive organs.*—Androecium: Present on disc florets only. Anther color: 14A. Pollen: Moderate. Pollen color: 14A. Gynoecium: Present on both ray and disc florets.

*Seed.*—Seed production has not been observed.

Disease resistance: Plants of the new Chrysanthemum have not been shown to be resistant to pathogens common to Chrysanthemums.

It is claimed:

1. A new and distinct cultivar of Chrysanthemum plant named 'Bold Yofelicia', as illustrated and described.

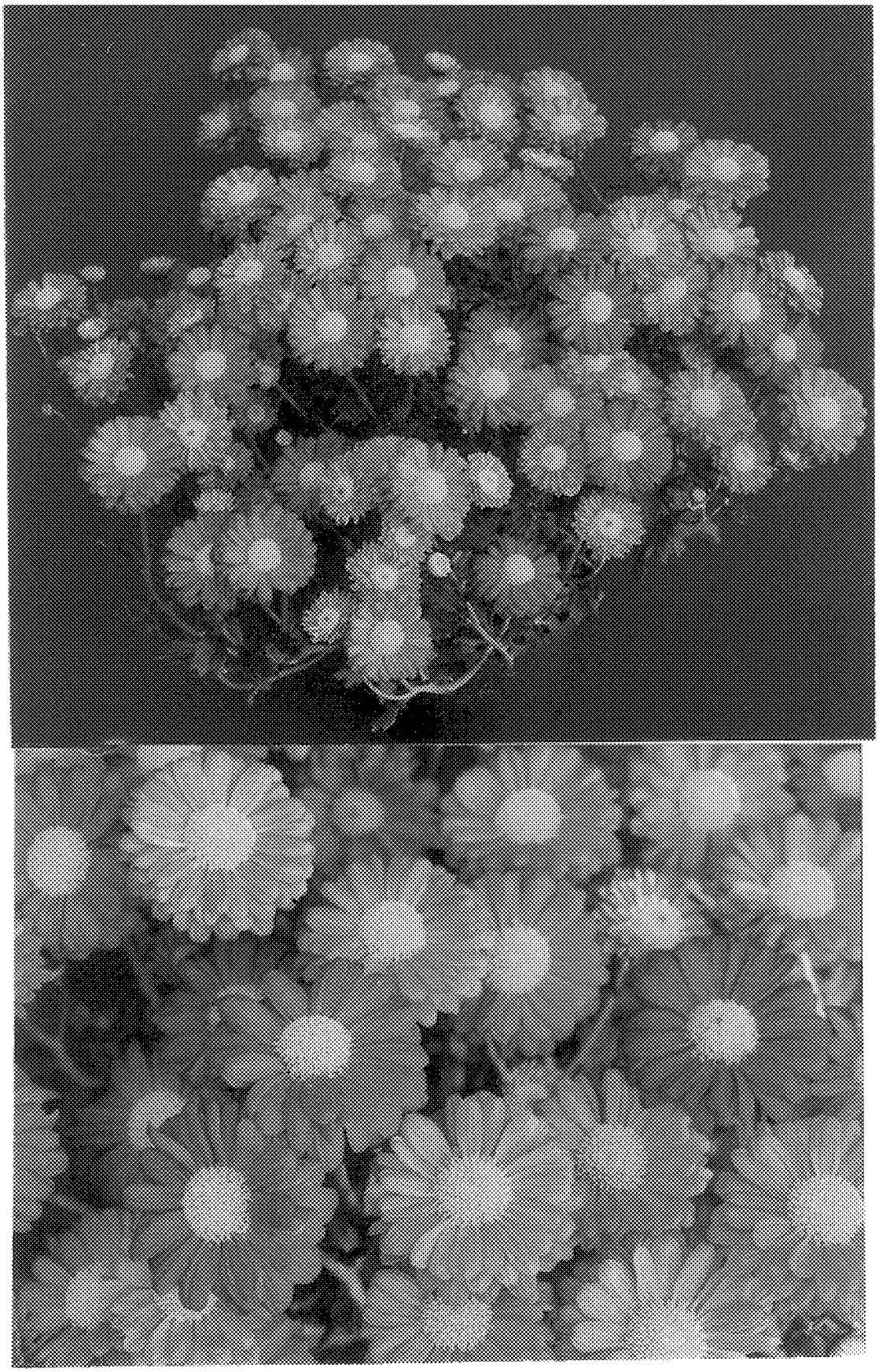

* * * * *